United States Patent [19]

Zinnen

[11] Patent Number: 4,721,806
[45] Date of Patent: Jan. 26, 1988

[54] PROCESS FOR SEPARATING 2,4-TOLUENE DIISOCYANATE FROM ISOMERS OF TOLUENE DIISOCYANATE

[75] Inventor: Hermann A. Zinnen, Evanston, Ill.

[73] Assignee: UOP Inc., Des Plaines, Ill.

[21] Appl. No.: 47,953

[22] Filed: May 8, 1987

Related U.S. Application Data

[63] Continuation-in-part of Ser. No. 915,826, Oct. 6, 1986, abandoned, which is a continuation of Ser. No. 781,561, Sep. 30, 1985, abandoned.

[51] Int. Cl.$^4$ ............................................. C07C 143/00
[52] U.S. Cl. ................................................... 560/352
[58] Field of Search ......................................... 560/352

[56] References Cited

U.S. PATENT DOCUMENTS

| | | |
|---|---|---|
| 3,069,470 | 12/1962 | Fleck et al. . |
| 4,061,662 | 12/1977 | Marans et al. . |
| 4,169,175 | 9/1979 | Marans et al. . |
| 4,246,187 | 1/1981 | Yabroff . |
| 4,270,013 | 5/1981 | Priegnitz et al. . |
| 4,467,126 | 8/1984 | Zinnen . |
| 4,480,129 | 10/1984 | Priegnitz et al. . |

FOREIGN PATENT DOCUMENTS 56-90579  5/1979  Japan .

OTHER PUBLICATIONS

59 Air Pollution Ind. Hyg., vol. 101, 1984, p. 309, Chem. Abst. 101:116099x.

*Primary Examiner*—Alan Siegel
*Attorney, Agent, or Firm*—Thomas K. McBride; John F. Spears, Jr.; Jack H. Hall

[57] ABSTRACT

This invention comprises a process for separating 2,4-toluene diisocyanate from a feed mixture with 2,6-toluene diisocyanate. The process comprises contacting the mixture at adsorption conditions with an adsorbent comprising a Y-type zeolite cation exchanged with a cation in the group Na, Ca, Li or Mg, thereby selectively adsorbing the 2,4-toluene diisocyanate. The remainder of the feed mixture is removed from the adsorbent and the adsorbed toluene diisocyanate isomer is recovered by desorption at desorption conditions with a desorbent material comprising toluene.

4 Claims, 4 Drawing Figures

PROCESS FOR SEPARATING 2,4-TOLUENE DIISOCYANATE FROM ISOMERS OF TOLUENE DIISOCYANATE

BACKGROUND OF THE INVENTION

This application is a continuation-in-part of U.S. Ser. No. 915,826, filed Oct. 6, 1986 now abandoned, which is a continuation of U.S. Ser. No. 781,561, filed Sept. 30, 1985, now abandoned.

FIELD OF THE INVENTION

The field of art to which this invention pertains is the solid bed adsorptive separation of isomers of toluene diisocyanate. More specifically, the invention relates to a process for separating 2,4-toluene diisocyanate from the other toluene diisocyanate isomers by employing a solid bed adsorption system.

BACKGROUND INFORMATION

The isomers, 2-4-toluene diisocyanate and 2,6-toluene diisocyanate are important starting materials for making polyurethanes which are useful in many applications as rigid or flexible forms or as fibers, e.g., insulation, soundproofing, interlinings for clothing and sleeping bags, cushions, spandex, etc.

It is common industrial practice to make polyurethane from a mixture of the isomers, 2,4- and 2,6-toluene diisocyanate (TDI), for example 80/20 or 65/35, derived from 2,4- and 2,6-toluene diisocyanate, because it is difficult and expensive to separate them by existing techniques. Current methods of separating the isomers involve crystallization and hence, are time-consuming. Moreover, polyurethanes synthesized from the pure 2,4- and 2,6-toluene diisocyanate have dramatically different properties compared to materials synthesized from mixtures. I have found that the tensile strength of polyurethane made of 2,4-toluene diisocyanate is greater than that of 2,6-toluene diisocyanate or any blend of the toluene diisocyanates and, in fact, increases as the level of 2,4-toluene diisocyante increases. Accordingly, it is desirable to separate the TDI isomers by an economical process.

It is well known in the separation art that certain crystalline aluminosilicates can be used to separate hydrocarbon types from mixtures thereof. Furthermore, X and Y zeolites have been employed in a number of processes to separate individual hydrocarbon isomers.

It is known from U.S. Pat. No. 3,069,470 to Fleck et al, to use type X zeolites for the separation of the meta isomer from other isomers of toluidine. From U.S. Pat. No. 4,480,129, it is known that X and Y type zeolites, exchanged with transition metals, are paraselective in a mixture of isomers of toluidine.

U.S. Pat. No. 4,061,662 discloses the adsorption of unreacted toluene diisocyanate from polyisocyanate with X-type zeolites. U.S. Pat. No. 4,169,175 discloses removal of less than 0.7% unreacted toluene diisocyanate from urethane prepolymers with X-type zeolites.

Yabroff U.S. Pat. No. 4,246,187 discloses a method for separating the 2,4- and 2,6- isomers of toluene diisocyanate involving steps of crystallizing and centrifuging.

In U.S. Pat. No. 3,575,820, it is disclosed that ortho isomers of toluene diisocyanate can be removed from toluene diisocyanate mixtures by incorporating aluminum oxide which will polymerize the ortho isomers, whereupon the non-vicinal isomers can be separated by distillation. Chemical Abstract 101:116099X (1984) discloses a treatment for removing toluene diisocyanate from waste gas by adsorption with activated carbon.

In Japanese Patent Application No. 56905/79, publicly disclosed on Nov. 20, 1980, it is disclosed that a solid adsorbent containing titanium oxide will selectively adsorb the para-isomer of toluidine.

It is known from U.S. Pat. No. 4,270,013 to Priegnitz et al that ortho-nitrotoluene may be separated from other nitrotoluene isomers by using a type-X zeolite containing at exchangeable cationic sites one cation selected from a group that includes potassium and barium. The specific desorbent materials disclosed by this reference are toluene and 1-hexanol. The separation of isomers of di-substituted benzenes with crystalline aluminosilicates having silica/alumina mole ratio of at least 12 is disclosed in my U.S. Pat. No. 4,467,126.

SUMMARY OF THE INVENTION

In brief summary, the invention is, in one embodiment, a process for separating 2,4-toluene diisocyanate from a mixture comprising 2,4-toluene diisocyanate and at least one isomer thereof, such as 2,6-toluene diisocyanate. The process comprises contacting the mixture at adsorption conditions with an adsorbent comprising a Y-type zeolite cation exchanged with a cation in the group Ca, Na, Li or Mg, thereby selectively adsorbing the 2,4-toluene diisocyanate thereon. The remainder of the feed mixture is then removed from the adsorbent and the adsorbed isomer recovered by desorption at desorption conditions with a desorbent material comprising toluene.

Other embodiments of our invention encompass details about feed mixtures, adsorbents, desorbent materials and operating conditions, all of which are hereinafter disclosed in the following discussion of each of the facets of the present invention.

DESCRIPTION OF THE INVENTION

Figure 1:
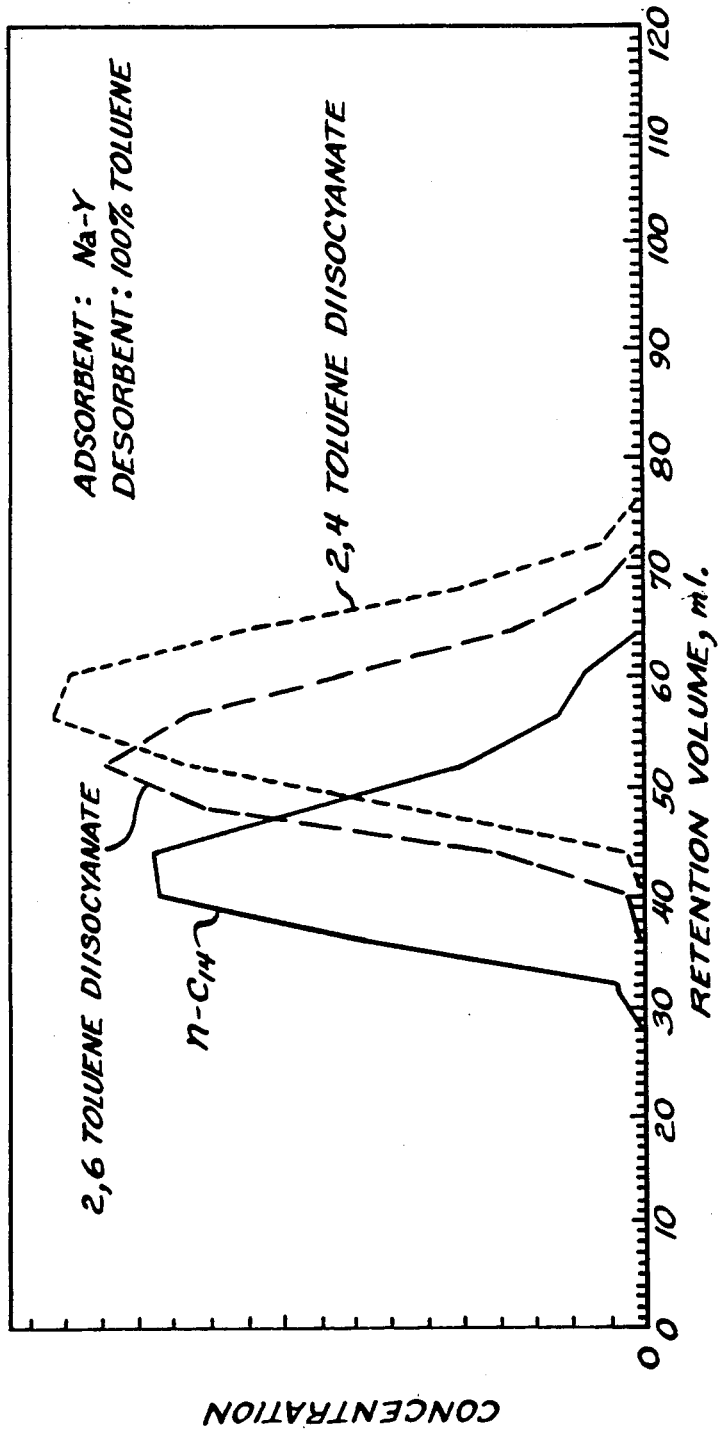
FIG. 1 is a plot showing the chromatographic separation of the 2,4- and 2,6-isomers of toluene diisocyanate by a Na-Y zeolitic adsorbent.

At the outset, the definitions of various terms used throughout the specification will be useful in making clear the operation, objects and advantages of our process.

A "feed mixture" is a mixture containing one or more extract components and one or more raffinate components to be separated by our process. The term "feed stream" indicates a stream of a feed mixture which passes to the adsorbent used in the process.

An "extract component" is a compound or type of compound that is more selectively adsorbed by the adsorbent while a "raffinate component" is a compound or type of compound that is less selectively adsorbed. In this process, 2,4-toluene diisocyanate is an extract component and 2,6-toluene diisocyanate is a raffinate component when the adsorbent is a Na-, Ca-, Li- or Mg-exchanged Y zeolite. In other cases, using other exchange ions, e.g., potassium, the roles are reversed, with the 2,6-toluene diisocyanate becoming the extract and 2,4-toluene diisocyanate becoming a raffinate component. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream and, preferably, at least a portion of the raffinate stream from the separation process are passed to separation means, typically fractionators, where at least a portion of the desorbent material is separated to produce an extract product and a raffinate product. The terms "extract product" and "raffinate product" mean products produced by the process containing, respectively, an extract component and a raffinate component in higher concentrations than those found in the extract stream and the raffinate stream. Although it is possible by the process of this invention to produce a high purity product at high recoveries, it will be appreciated that an extract component is never completely adsorbed by the adsorbent, nor is a raffinate component completely nonadsorbed by the adsorbent. Therefore, varying amounts of a raffinate component can appear in the extract stream and, likewise, varying amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of the more selectively adsorbed isomer to that of the less selectively adsorbed isomer will be lowest in the raffinate stream, next highest in the feed mixture, and the highest in the extract stream.

The term "selective pore volume" of the adsorbent is defined as the volume of the adsorbent which selectively adsorbs an extract component from the feed mixture. The term "non-selective void volume" of the adsorbent is the volume of the adsorbent which does not selectively retain an extract component from the feed mixture. This volume includes the cavities of the adsorbent which contain no adsorptive sites and the interstitial void spaces between adsorbent particles. The selective pore volume and non-selective void volume are generally expressed in volumetric quantities and are of importance in determining the proper flow rates of fluid required to be passed into an operational zone for efficient operations to take place for a given quantity of adsorbent. When adsorbent "passes" into an operational zone employed in one embodiment of this process, its non-selective void volume together with its selective pore volume carries fluid into that zone. The non-selective void volume is utilized in determining the amount of fluid which should pass into the same zone in a countercurrent direction to the adsorbent to displace the fluid present in the nonselective void volume. If the fluid flow rate passing to a zone is smaller than the non-selective void volume rate of adsorbent material passing into that zone, there is a net entrainment of liquid into the zone by the adsorbent. Since this net entrainment is a fluid present in the non-selective void volume of the adsorbent, it in most instances comprises less selectively retained feed components. The selective pore volume of an adsorbent can in certain instances adsorb portions of raffinate material from the fluid surrounding the adsorbent since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

The prior art has recognized that certain characteristics of adsorbents are highly desirable, if not absolutely necessary, to the successful operation of a selective adsorption process. Such characteristics are equally important to this process. Among such characteristics are: adsorptive capacity for some volume of an extract component per volume of adsorbent; the selective adsorption of an extract component with respect to a raffinate component and the desorbent material; and sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of a separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), is defined as the ratio of the two components of the adsorbed phase over the ratio of the same two components in the unadsorbed phase at equilibrium conditions. Relative selectivity is shown as Equation 1, below:

Equation 1

$$\text{Selectivity} = (B) = \frac{[\text{vol. percent } C/\text{vol. percent } D]_A}{[\text{vol. percent } C/\text{vol. percent } D]_U}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases. Where selectivity of two components approaches 1.0, there is no preferential adsorption of one component by the adsorbent with respect to the other; they are both adsorbed (or non-adsorbed) to about the same degree with respect to each other. As the (B) becomes less than or greater than 1.0, there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D.

The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

Adsorbents to be used in the process of this invention will comprise specific crystalline aluminosilicates. Particular crystalline aluminosilicates encompassed by the present invention include crystalline aluminosilicate cage structures in which the alumina and silica tetrahedra are intimately connected in an open three-dimensional network to form cage-like structures with window-like pores of about 8 Å free diameter. The tetrahedra are crosslinked by the sharing of oxygen atoms with spaces between the tetrahedra occupied by water molecules prior to partial or total dehydration of this zeolite. The dehydration of the zeolite results in crystals interlaced with cells having molecular dimensions and thus the crystalline aluminosilicates are often referred to as "molecular sieves", particularly when the separation which they effect is dependent essentially upon differences between the sizes of the feed molecules as, for instance, when smaller normal paraffin molecules are separated from larger isoparaffin molecules by using a particular molecular sieve.

In hydrated form, the crystalline aluminosilicates used in the process of this invention generally encompass those zeolites represented by the Formula 1 below:

Formula 1

$$M_{2/n}O:Al_2O_3:wSiO_2:yH_2O$$

where "M" is a cation which balances the electrovalence of the aluminumcentered tetrahedra and which is generally referred to as an exchangeable cationic site, "n" represents the valence of the cation, "w" represents the moles of $SiO_2$, and "y" represents the moles of water. The generalized cation "M" may be monovalent, divalent or trivalent or mixtures thereof.

The prior art has generally recognized that adsorbents comprising X and Y zeolites can be used in certain adsorptive separation processes. These zeolites are described and defined in U.S. Pat. Nos. 2,882,244 and 3,130,007, respectively, incorporated herein by refernce thereto. The Y zeolite in the hydrated or partially hydrated form can be represented in terms of mole oxides as in Formula 2 below:

Formula 2

$$(0.9 \pm 0.2)M_{2/n}O:Al_2O_3:wSiO_2:yH_2O$$

where "M" is at least one cation having a valence not more than 3, "n" represents the valence of "M", "w" is a value greater than about 3 up to about 6, and "y" is a value up to about 9 depending upon the identity of "M" and the degree of hydration of the crystal. The $SiO_2/Al_2O_3$ mole ratio for Y zeolites can thus be from about 3 to about 6. The cation "M" may be one or more of a variety of cations such as a hydrogen cation, an alkali metal cation, an alkaline earth cation or other selected cations, and is generally referred to as an exchangeable cationic site but, as the Y zeolite is initially prepared, the cation "M" is usually predominately sodium. A Y zeolite containing predominately sodium cations at the exchangeable cationic sites is referred to as a sodium-Y zeolite.

Cations occupying exchangeable cationic sites in the zeolite may be replaced with other cations by ion exchange methods well known to those having ordinary skill in the field of crystalline aluminosilicates. Such methods are generally performed by contacting the zeolite or an adsorbent material containing the zeolite with an aqueous solution of the soluble salt of the cation or cations desired to be placed upon the zeolite. After the desired degree of exchange takes place, the sieves are removed from the aqueous solution, washed, and dried to a desired water content. By such methods the sodium cations and any non-sodium cations which might be occupying the exchangeable sites as impurities in a zeolite can be partially or essentially completely replaced with other cations. The zeolite used in the process of this invention contains cations at exchangeable cationic sites selected from the group of metals Na, Ca, Li or Mg.

Typically, adsorbents used in separative processes contain zeolite crystals dispersed in an amorphous material or inorganic matrix. The zeolite will typically be present in the adsorbent in amounts ranging from about 75 to about 98 wt. % based on volatile-free composition. Volatile-free compositions are generally determined after the adsorbent has been calcined at 9° C. in order to drive off all volatile matter. The remainder of the adsorbent will generally be the inorganic matrix material such as silica, titania, or alumina or mixtures thereof, or compounds, such as clays, which material is present in intimate mixture with the small particles of the zeolite material. This matrix material may be an adjunct of the manufacturing process for zeolite (for example, intentionally incomplete purification of either zeolite during its manufacture) or it may be added to relatively pure zeolite, but in either case its usual purpose is as a binder to aid in forming or agglomerating the hard crystalline particles of the zeolite. Normally, the adsorbent will be in the form of particles such as extrudates, aggregates, tablets, macrospheres or granules having a desired particle size range. The typical adsorbent will have a particle size range of about 16-60 mesh (Standard U.S. Mesh). An example of a zeolite used in adsorbents known to the art, either as is or after cation exchange, is "SK-40", available from the Linde Company, Tonawanda, New York. "SK-40" contains Y zeolite.

Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is just slightly greater than 1.0, it is preferred that such selectivity be reasonably greater than 1.0. Like relative volatility, the higher the selectivity, the easier the separation is to perform. Higher selectivities permit a smaller amount of adsorbent to be used.

Desorbent materials used in various prior art adsorptive separation processes vary depending upon such factors as the type of operation employed. In the swing bed system in which the selectively adsorbed feed component is removed from the adsorbent by a purge stream desorbent, selection is not as critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Desorbent materials should additionally be substances which are easily separable from the feed mixture that is passed into the process. Both the raffinate stream and the extract stream are removed from the adsorbent in admixture with desorbent material and without a method of separating at least a portion of the desorbent material, the purity of the extract product and the raffinate product would not be very high nor would the desorbent material be available for reuse in the process. It is therefore contemplated that any desorbent material used in this process will preferably have a substantially different average boiling point than that of the feed mixture to allow separation of at least a portion of desorbent material from feed components in the extract and raffinate streams by simple fractional distillation, thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture. Finally, desorbent materials should also be materials which are readily available and therefore reasonable in cost. In the preferred isothermal, isobaric, liquid-phase operation of the process of our invention, we have found that toluene will result in selectivity for the 2,4-toluene diisocyanate when a Y zeolite is exchanged for Na, Li, Ca and Mg.

The adsorbent may be employed in the form of a dense compact fixed bed which is alternatively contacted with the feed mixture and desorbent materials. In the simplest embodiment of the invention, the adsorbent is employed in the form of a single static bed in which case the process is only semi-continuous. In another embodiment, a set of two or more static beds may be employed in fixed bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Moving bed or simulated moving bed flow systems, however, have a much greater separation efficiency than fixed bed systems and are therefore preferred. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. The operating principles and sequence of such a flow system are described in U.S. Pat. No. 2,985,589 to D. B. Broughton, incorporated herein by refernce. In such a system, it is the progressive movement of multiple liquid access points down a molecular sieve chamber that simulates the upward movement of molecular sieve contained in the chamber. Reference can also be made to a paper entitled "Continuous Adsorptive Processing - A New Separation Technique" by D. B. Broughton presented at the 34th Annual Meeting of the Society. of Chemical Engineers at Tokyo, Japan on Apr. 2, 1969, incorporated herein by reference, for further explanation of the simulated moving bed countercurrent process flow scheme.

Another embodiment of a simulated moving bed flow system suitable for use in the process of the present invention is the cocurrent high efficiency simulated moving bed process disclosed in our assignee's U.S. Pat. No. 4,402,832, incorporated by reference herein in its entirety.

It is contemplated with any flow scheme used to carry out the present invention that at least a portion of the extract output stream will pass into a separation means wherein at least a portion of the desorbent material can be separated to produce an extract product containing a reduced concentration of desorbent material. Preferably, but not necessary to the operation of the process, at least a portion of the raffinate output stream will also be passed to a separation means wherein at least a portion of the desorbent material can be separated to produce a desorbent material stream which can be reused in the process and a raffinate product containing a reduced concentration of desorbent material. The separation means will typically be a fractionation column, the design and operation of which is well known to the separation art.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Desorption conditions will thus include, as hereinbefore mentioned, a pressure sufficient to maintain liquid-phase. Adsorption conditions will include the same range of temperatures and pressures as used for desorption conditions.

A static test procedure and apparatus may be employed to test various adsorbents with a particular feed mixture to determine the relative retention by the adsorbent of each component of the mixture. The procedure involves mixing together equal quantities of each component, the relative retention of which is to be determined, and a convenient solvent or desorbent material. A desorbent is selected that will have a boiling point well separated from those of the isomers being tested. The resulting solution is then placed in a vessel with a quantity of the appropriate adsorbent and is allowed to remain, with occasional stirring, for about 24 hours. The solution is then analyzed for each component and the relative retention thereof is determined in terms of the ratio, R, of the less strongly adsorbed component to the more strongly adsorbed component, the relative retention of the more strongly retained component being greater, the higher the above ratio.

A dynamic testing apparatus is employed to test various adsorbents with a particular feed mixture and desorbent material to measure the adsorption characteristics of retention capacity and exchange rate. The apparatus consists of a helical adsorbent chamber of approximately 70–80 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine data for various adsorbent systems. The adsorbent is filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent material is injected for a duration of several minutes. Desorbent material flow is resumed, and the tracer and the extract component or the raffinate component (or both) are eluted as in a liquid-solid chromatographic operation. The effluent can be analyzed on-stream or alternatively, effluent samples can be collected periodically and later analyzed separately by analytical equipment and traces of the envelopes or corresponding component peaks developed.

From information derived from the test, adsorbent performance can be rated in terms of void volume, retention volume for an extract or a raffinate component, and the rate of desorption of an extract component from the adsorbent. The retention volume of an extract or a raffinate component may be characterized by the distance between the center of the peak envelope of the extract or raffinate component and the center of the peak envelope of the tracer component or some other known reference point. It is expressed in terms of the volume in cubic centimeters of desorbent material pumped during this time interval represented by the distance between the peak envelopes. The rate of exchange of an extract component with the desorbent material can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is again the volume of desorbent material pumped during this time interval.

The following non-limiting examples are presented to illustrate the process of the present invention and are not intended to unduly restrict the scope of the claims attached hereto.

EXAMPLE 1

A number of static tests were performed to demonstrate that it was possible to separate the isomers by an adsorptive process. In this case, because the analytical method will not completely resolve the isomers of TDI, the adsorption test was conducted with an analogous compound, phenyl isocyanate. Phenyl isocyanate, which can be analytically resolved from both the 2,4-toluene diisocyanate and 2,6-toluene diisocyanate, is separately mixed with each of the isomers and 2 sets of tests are conducted for each adsorbent. The relative static selectivity A of the isomers is obtained by first calculating that of phenyl isocyanate with each of the isomers as follows:

$$A_{PI/2,4} = \frac{PI(A)/2,4(A)}{PI(U)/2,4(U)}$$

$$A_{2,6/PI} = \frac{2,6(A)/PI(A)}{2,6(U)/PI(U)}$$

Then, $$A_{2,6/2,4} = A_{PI/2,4} \times A_{2,6/PI}$$

In an inert atmosphere, a stock solution of each tolene diisocyanate (TDI) isomer with phenyl isocyanate and isooctane was made up as follows and tested separately:

| 2,4-TDI or 2,6-TDI | 5.88 vol. % |
| phenyl isocyanate | 5.88 vol. % |
| isooctane | balance |

In all the static tests, the volume ratio of stock solution to adsorbent was 1.5. The temperature was 25° C. The stock solution and adsorbent were combined in a flask and the amount of each isomer left in the raffinate was determined and the static selectivity, A, of 2,6-TDI/2,4-TDI was calculated in the manner just described for a number of adsorbents. The results are as follows:

| Adsorbent | A 2,6-/2,4- |
|---|---|
| BaK—X | no adsorption |

-continued

| Adsorbent | A 2,6-/2,4- |
|---|---|
| K—Y | 1.63 |
| Na—Y | 0.79 |
| Li—Y | 0.71 |
| Mg—Y | 0.60 |

These tests show that 2,4-TDI is selectively adsorbed by Na-Y, Li-Y and Mg-Y, while 2,6-TDI is selectively adsorbed by K-Y. Hence, these isomers may be separated by our adsorptive process. BaK-X showed no adsorption of either isomer. Several of these adsorbents also underwent the pulse test as described in the next example, confirming the results of the static test.

EXAMPLE 2

The previously described pulse test apparatus was used to obtain data for this example using a sodium exchanged Y zeolite. The liquid temperature was 153° C. and the flow was up the column at the rate of 1.2 cc/min. The feed stream comprised a 2.6 cc pulse of a solution containing 1 cc of a 65/35 mixture of 2,4- and 2,6-TDI, and 0.8 cc of n-$C_{14}$ tracer. The column was packed with clay bound adsorbent of 30-60 mesh particle size. The desorbent was 100% toluene.

The selectivity (B), as earlier described, was calculated from the trace of the peaks generated for the components. The results of this example are shown in FIG. 1. The selectivity, $B_{2,4/2,6} = 1.40$.

EXAMPLES 3-4

Figure 2:
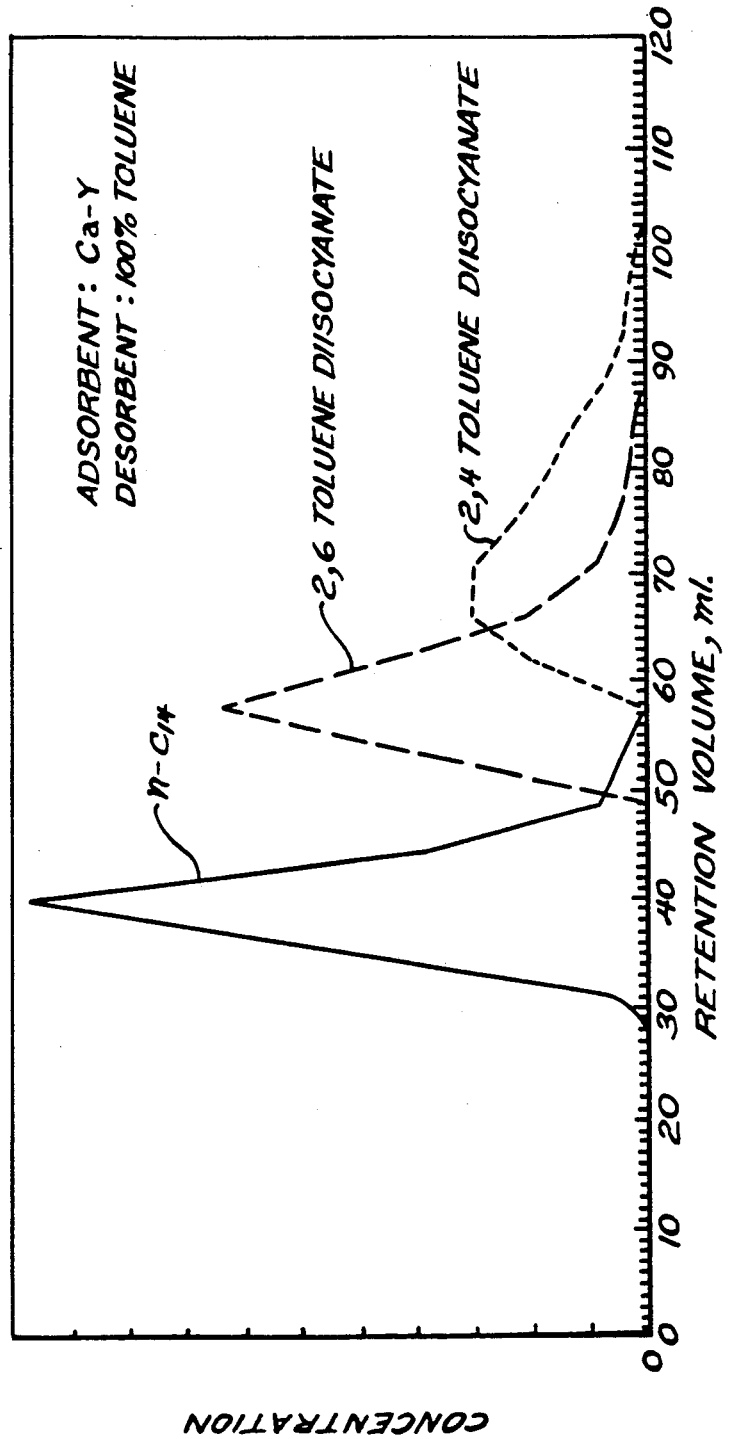
FIG. 2 is a plot showing the chromatographic separation of the same isomers by a Ca-Y zeolitic adsorbent.
Figure 3:
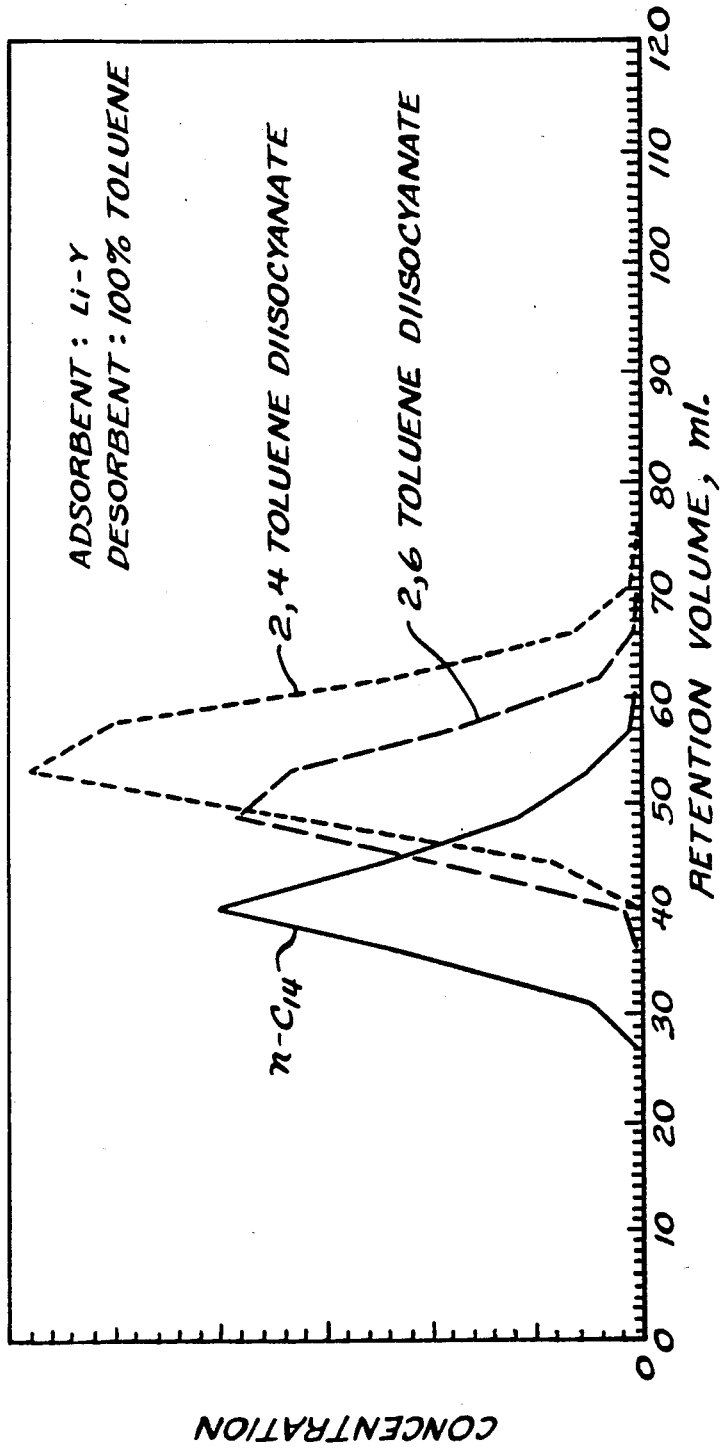
FIG. 3 is a plot showing the chromatographic separation of the same isomers by a Li-Y zeolitic adsorbent.

Further pulse tests were done, using the same conditions as Example 2 except that the temperatures and adsorbents were different as set forth in the following table, together with the selectivity $(B)_{2,4/2,6}$ calculated from the trace of the peaks in FIGS. 2 and 3:

| Example | Adsorbent | Liq. Temp. | B2,4/2,6 | Desorbent |
|---|---|---|---|---|
| 3 | Ca—Y | 150° C. | 1.72 | toluene |
| 4 | Li—Y | 155° C. | 1.44 | toluene |

EXAMPLE 5

The previously described pulse test apparatus was used to obtain data for this example using a sodium exchanged Y zeolite. The liquid temperature was 100° C. and the flow was down the column at the rate of 1.26 cc/min. The feed stream comprised a 2.6 cc pulse of a solution containing 2 cc of a 80/20 mixture of 2,4- and 2,6-TDI, and 0.5 cc of n-$C_{14}$ tracer with the balance desorbent. The column was packed with clay bound adsorbent of 30-60 mesh particle size. The desorbent was 100% toluene.

Figure 4:
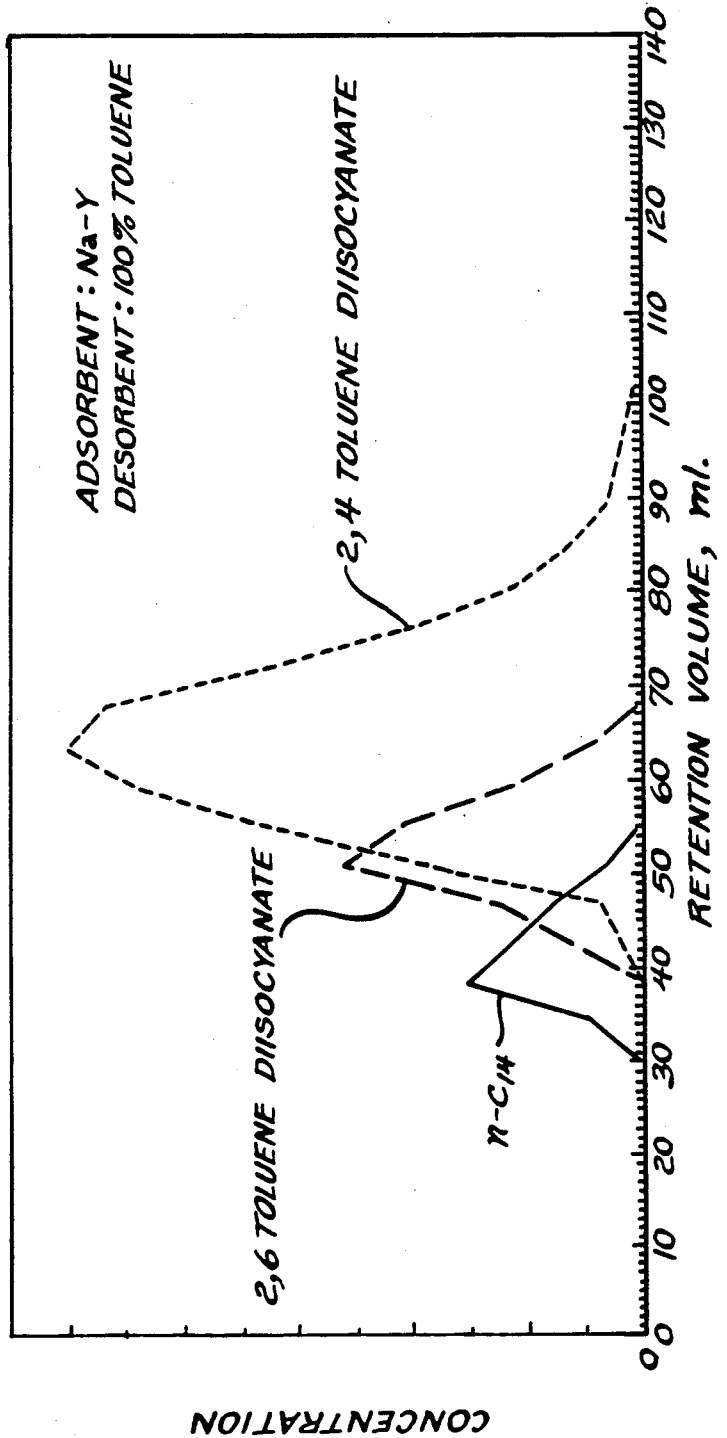
FIG. 4 is a plot showing the chromatographic separation of the same isomers by a Na-Y zeolitic adsorbent.

The selectivity (B), as earlier described, was calculated from the trace of the peaks generated for the components. The results of this example are shown in FIG. 4. The selectivity, $B_{2,4/2,6} = 1.90$.

In general, the above data does show that the present invention provides a 2,4-toluene diisocyanate selective system with Na, Ca, Mg and Li- Y-type zeolite adsorbents with adequate selectivities for the commercial use of the separation of the present invention.

What is claimed is:

1. A process for separating 2,4-toluene diisocyanate from a feed mixture comprising 2,4-toluene diisocyanate and 2,6-toluene diisocyanate, said process comprising contacting said mixture at adsorption conditions with an adsorbent comprising a Y- type zeolite, cation exchanged with a cation from the group Na, Ca, Li and Mg, thereby selectively adsorbing said 2,4-toluene diisocyanate-, removing the remainder of said mixture from said adsorbent, and then recovering said adsorbed 2,4-toluene diisocyanate by desorption at desorption conditions with a desorbent material comprising toluene.

2. The process of claim 1 wherein said adsorption and desorption conditions include a temperature within the range of from about 20° C. to about 200° C. and a pressure sufficient to maintain liquid phase.

3. The process of claim 1 wherein said process is effected with a simulated moving bed flow system.

4. The process of claim 1 wherein said process is effected with a static bed system.

* * * * *